(12) United States Patent
Miyazaki

(10) Patent No.: US 9,579,041 B2
(45) Date of Patent: Feb. 28, 2017

(54) SEMI-AUTOMATED NON-CONTRAST MAGNETIC RESONANCE ANGIOGRAPHY (MRA)

(75) Inventor: Mitsue Miyazaki, Mount Prospect, IL (US)

(73) Assignee: TOSHIBA MEDICAL SYSTEMS CORPORATION, Otawara-Shi, Tochigi-Ken (JP)

(*) Notice: Subject to any disclaimer, the term of this patent is extended or adjusted under 35 U.S.C. 154(b) by 214 days.

(21) Appl. No.: 13/479,680

(22) Filed: May 24, 2012

(65) Prior Publication Data

US 2013/0317348 A1 Nov. 28, 2013

(51) Int. Cl.
*A61B 5/055* (2006.01)
*A61B 5/20* (2006.01)
*A61B 5/00* (2006.01)

(52) U.S. Cl.
CPC .......... *A61B 5/055* (2013.01); *A61B 5/0037* (2013.01); *A61B 5/201* (2013.01)

(58) Field of Classification Search
CPC .................. A61B 5/055; A61B 2019/5236
USPC ........................... 600/410, 413, 419
See application file for complete search history.

(56) References Cited

U.S. PATENT DOCUMENTS

| | | | |
|---|---|---|---|
| 2008/0071166 A1* | 3/2008 | Miyazaki | 600/419 |
| 2009/0292197 A1* | 11/2009 | Fuderer | 600/410 |
| 2011/0071382 A1 | 3/2011 | Miyazaki et al. | |
| 2011/0080170 A1* | 4/2011 | Miyazaki | 324/309 |

FOREIGN PATENT DOCUMENTS

| | | |
|---|---|---|
| JP | 2000-342555 | 12/2000 |
| JP | 2010-155021 | 7/2010 |
| JP | 2011-143236 | 7/2011 |

OTHER PUBLICATIONS

Albert, Timothy et al, Time-Spatial Labeling Inverse Pulse: Safe, Simple and Effective Non-Contrast MR Angiography, 2010, Toshiba America Medical Systems, Inc, pp. 1-7.*
Parienty, et al., "Renal Artery Stenosis Evaluation in chronic Kidney Disease Patients; Nonenhanced Time-Spatial Labeling Inversion-Pulse Three-dimensional MR Angiography with Regulated Breathing versus DSA," *Radiology*, vol. 259, No. 2, pp. 592-601 (May 2011).
International Search Report issued Aug. 13, 2013 in PCT/JP2013/064538.

* cited by examiner

*Primary Examiner* — Rochelle Turchen
(74) *Attorney, Agent, or Firm* — Nixon & Vanderhye P.C.

(57) ABSTRACT

A magnetic resonance imaging (MRI) system semi-automatically performs non-contrast magnetic resonance angiography (MRA). An operator display and control input port configures the MRI system to effect semi-automated non-contrast MRA imaging with spatially selective tag and venous suppression RF pulses and/or black blood time interval (BBTI) parameters in a non-contrast MRA data acquisition sequence where such parameters are automatically determined within predetermined, respectively corresponding, spatial regions of patient anatomy. Such automatically determined non-contrast MRA imaging parameters may be entirely automatically set and used or, alternatively, may be displayed to an operator for acceptance and/or change before being used.

24 Claims, 10 Drawing Sheets

SEMI-AUTOMATED NON-CONTRAST MAGNETIC RESONANCE ANGIOGRAPHY (MRA)

FIELD

The subject matter below relates generally to magnetic resonance imaging (MRI) apparatus and process. In particular, the MRI apparatus and method described below involve magnetic resonance angiography (MRA).

DETAILED DESCRIPTION

Figure 1:
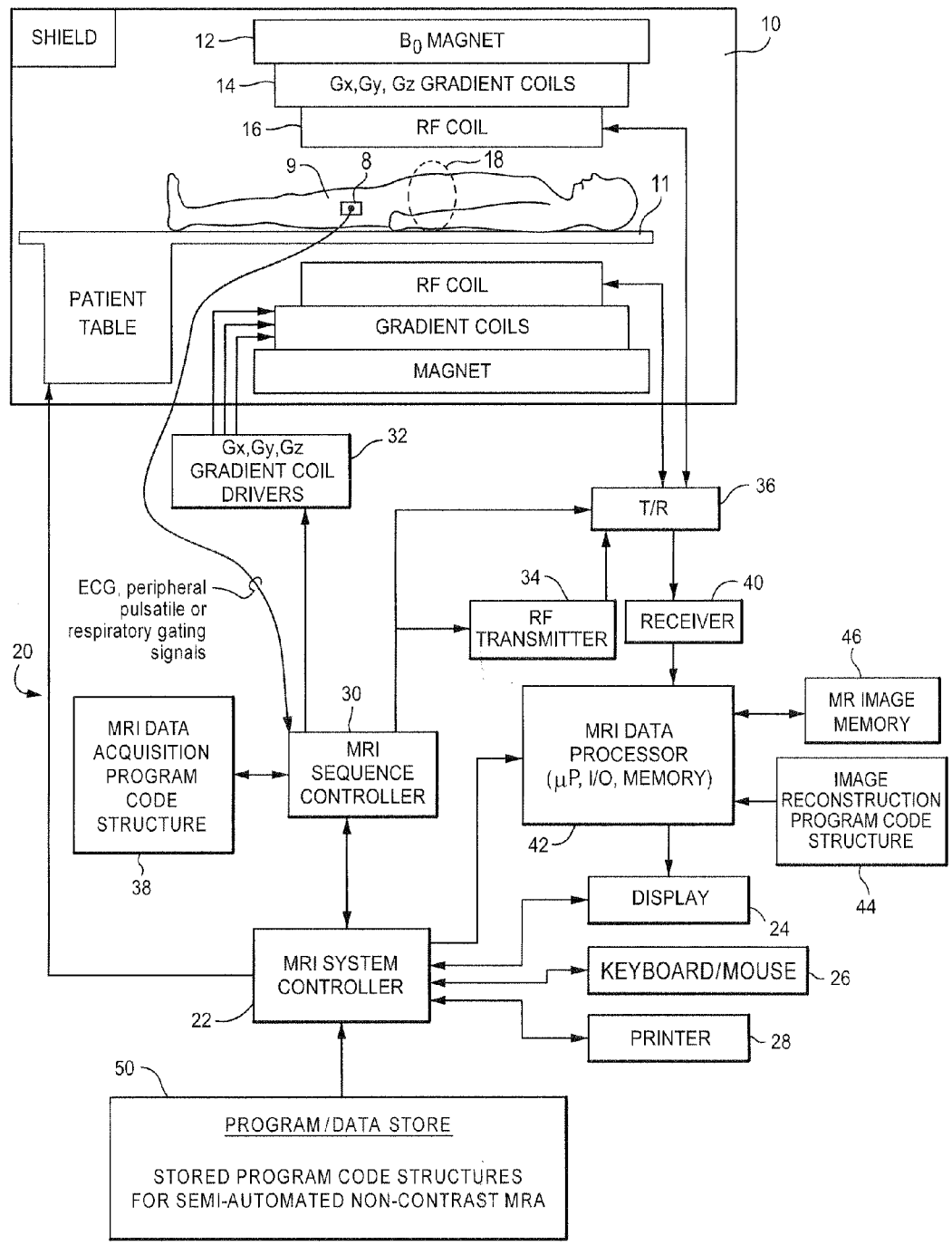
FIG. 1 is a high-level schematic block diagram of an exemplary MRI system embodiment configured to provide semi-automated non-contrast MRA.

The MRI system shown in FIG. 1 includes a gantry 10 (shown in schematic cross-section) and various related system components 20 interfaced therewith. At least the gantry 10 is typically located in a shielded room. The MRI system geometry depicted in FIG. 1 includes a substantially coaxial cylindrical arrangement of the static field Bo magnet 12, a Gx, Gy and Gz gradient coil set 14 and an RF coil assembly 16. Along the horizontal axis of this cylindrical array of elements is an imaging region 18 shown as substantially encompassing the anatomy of interest for a patient 9 (e.g., the abdomen for renal MRA) supported by a patient bed or table 11.

An MRI system controller 22 has input/output ports connected to display 24, keyboard/mouse 26 and printer 28. As will be appreciated, the display 24 may be of the touch-screen variety so that it provides control inputs as well.

The MRI system controller 22 interfaces with MRI sequence controller 30 which, in turn, controls the Gx, Gy and Gz gradient coil drivers 32, as well as RF transmitter 34 and transmit/receive switch 36 (if the same RF coil is used for both transmission and reception). As those skilled in the art will appreciate, one or more suitable physiological transducers 8 may be affixed to the patient's body to provide ECG (electrocardiogram), respiratory and/or peripheral pulsatile gating signals to the MRI sequence controller 30. The MRI sequence controller 30 also has access to suitable program code structure 38 for implementing MRI data acquisition sequences already available in the repertoire of the MRI sequence controller 30—e.g., to generate non-contrast MRA (magnetic resonance angiography) and/or MRV (magnetic resonance venography) and/or blood perfusion into tissue images using operator and/or system inputs defining particular MRI data acquisition sequence parameters.

The MRI system 20 includes an RF receiver 40 providing input to data processor 42 so as to create processed image data which may be sent to display 24. The MRI data processor 42 is also configured for access to image reconstruction program code structure 44 and to MR (magnetic resonance) image memory 46 (e.g., for storing MR image data derived from processing in accordance with the exemplary embodiments and the image reconstruction program code structure 44).

Also illustrated in FIG. 1 is a generalized depiction of an MRI system program/data store 50 where stored program code structures (e.g., for semi-automated non-contrast MRA, a related graphical user interface (GUI), operator inputs to same, etc.) are stored in computer readable storage media accessible to the various data processing components of the MRI system. As those in the art will appreciate, the program store 50 may be segmented and directly connected, at least in part, to different ones of the system 20 processing computers having most immediate need for such stored program code structures in their normal operation (i.e., rather than being commonly stored and connected directly to the MRI system controller 22).

Indeed, as those skilled in the art will appreciate, the FIG. 1 depiction is a very high level simplified diagram of a typical MRI system with some modifications so as to practice exemplary embodiments to be described hereinbelow. The system components can be divided into different logical collections of "boxes" and typically comprise numerous digital signal processors (DSP), microprocessors, special purpose processing circuits (e.g., for fast A/D conversions, fast Fourier transforming, array processing, etc.). Each of those processors is typically a clocked "state machine" wherein the physical data processing circuits progress from one physical state to another upon the occurrence of each clock cycle (or predetermined number of clock cycles).

Not only does the physical state of processing circuits (e.g., CPUs, registers, buffers, arithmetic units, etc.) progressively change from one clock cycle to another during the course of operation, the physical state of associated data storage media (e.g., bit storage sites in magnetic storage media) is transformed from one state to another during operation of such a system. For example, at the conclusion of an MR imaging reconstruction process, an array of computer-readable accessible data value storage sites (e.g., multi-digit binary representations of pixel values) in physical storage media will be transformed from some prior state (e.g., all uniform "zero" values or all "one" values) to a new state wherein the physical states at the physical sites of such an array (e.g., of pixel values) vary between minimum and maximum values to represent real world physical events and conditions (e.g., the tissues of a patient over an imaged region space). As those in the art will appreciate, such arrays of stored data values represent and also constitute a physical structure—as does a particular structure of computer control program codes that, when sequentially loaded into instruction registers and executed by one or more CPUs of the MRI system 20, cause a particular sequence of operational states to occur and be transitioned through within the MRI system.

The exemplary embodiments described below provide improved ways to acquire and/or process MRI data acquisitions and/or to generate and display MR images.

As explained by Parienty, et al., in *Radiology*, Vol. 259, No. 2, May 2011 (*Renal Artery Stenosis Evaluation in Chronic Kidney Disease Patients: Nonenhanced Time-Spatial Labeling Inversion-Pulse Three-dimensional MR Angiography with Regulated Breathing versus DSA*), hereby incorporated by reference, the flow-in balanced SSFP (steady state pulse precession) technique (Time-SLIP (time spatial labeling Inversion Pulse) TrueSSFP) applies a spatially selective inversion pulse (tag pulse) on a vasculature of interest to invert spins of blood and background tissues in a selected region prior to data sampling. Blood flowing from the aorta into the thus tagged region has a constant "bright blood" high signal intensity. Best blood-to-background contrast is obtained at an inversion time near the null point of the earlier inverted background signal (i.e., as it decays back toward its quiescent state in the static Bo field). An optimal blood inflow time should also allow the in-flowing untagged (bright) blood to travel far enough into the tagged region to replace the out-flowing previously inverted low signal level (black) blood in the vasculature of interest. For renal arteries, a flow-in technique is most commonly used with a three-dimensional balanced SSFP (flow-in balanced SSFP) sequence using respiratory gating. A blood travel time of approximately 1100 msec may be most effective in suppressing the signal of the renal medulla (i.e., since the kidney tissue has high water content, its T1 NMR parameter causes inverted nuclei to reach a null point of longitudinal magnetization at about 1100 ms); hence, the optimal blood travel time for the renal arteries may be between about 1100 and 1500 msec. A longer blood travel time will, of course, reduce contrast between renal arteries and the background; however, it may be required in patients with very slow blood flow. A conventional chemical shift-selective fat-saturation pulse is preferably included to further suppress the fat signal.

Figure 2:
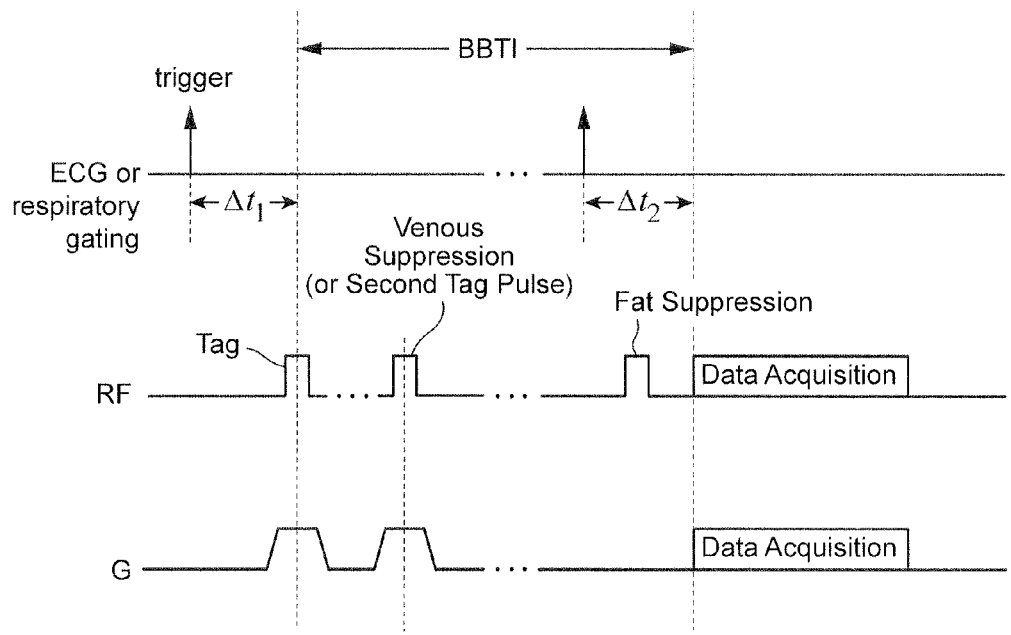
FIG. 2 is a schematic depiction of an exemplary MRA data acquisition sequence "shot" for use in FIG. 1.

As depicted in FIG. 2, a spatially selective RF tag pulse is applied at a desired trigger phase (i.e., $\Delta t_1$ from a desired (cardiac, respiratory or peripheral pulsatile) trigger point) followed by a subsequent spatially selective RF venous suppression pulse and then by a conventional non-spatially selective RF fat suppression pulse and a conventional MRA image data acquisition sequence "shot". As depicted, the data acquisition sequence may begin at a desired phase (e.g., a varying time slip $\Delta t_2$ from a trigger point). As those in the art will appreciate, the schematic depiction in FIG. 2 omits many conventional details of controlled magnetic gradient pulses, RF pulses, etc., during repeated data acquisition shot cycles over plural repetition intervals TR. Typically, a number of NMR (nuclear magnetic resonance) spin echoes are acquired during each data acquisition sequence cycle or "shot" so as to collectively acquire sufficient k-space data for plural slice images of an imaged region (e.g., a multi-slice data acquisition sequence).

Figure 3:
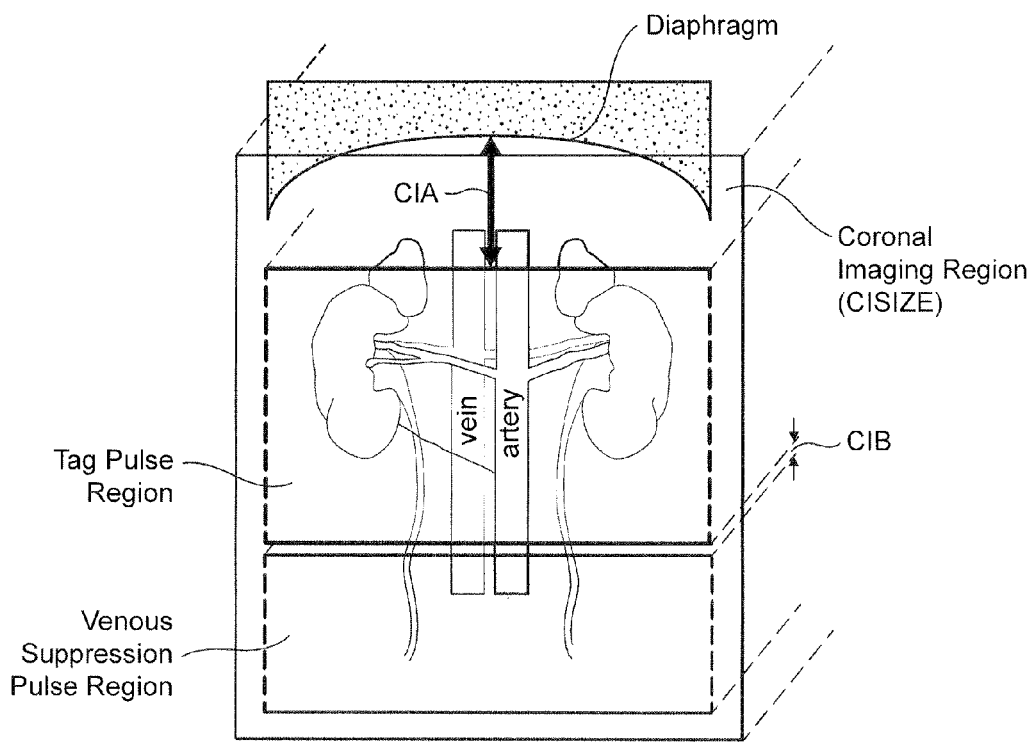
FIG. 3 is a schematic diagram of patient diaphragm and kidney anatomy, as well as tag pulse and venous suppression pulse regions for coronal imaging in accordance with an exemplary embodiment for semi-automated non-contrast renal MRA.
Figure 4:
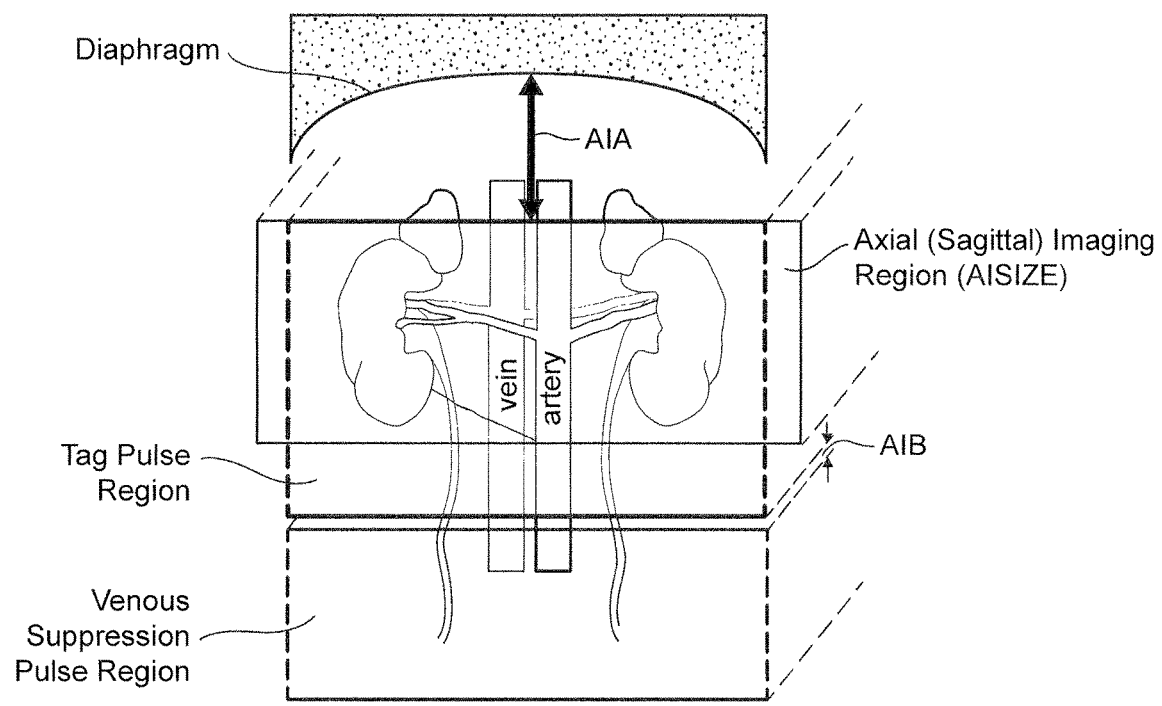
FIG. 4 is similar to FIG. 3, except that it depicts the relative arrangement of tag pulse and venous suppression pulse regions for axial (sagittal) imaging in accordance with an exemplary embodiment.

FIG. 3 shows an imaging plan for flow-in balanced SSFP imaging of the renal arteries. To reduce the signal of undesired inflowing blood, such as venous flow in the vena cava, a pre-saturation band pulse region is positioned just below the tagging pulse region. The tagging pulse region must include the vasculature of interest and its "top" edge must thus be placed above the superior poles of both kidneys, to reduce travel distance of untagged blood flowing into the tagged region. If the right and left kidneys are not horizontally aligned, the tagging pulse region can be rotated. Otherwise, a longer blood travel time is required at the expense of lower contrast between arterial blood and the medulla tissue. If the blood flow is very slow, the tagging pulse region can be positioned closer to the main renal arteries, at the expense of not allowing visualization of distal branches in the superior poles (which may not be therapeutically relevant).

As those in the art will appreciate, the left and right sides of the tag pulse and venous suppression pulse regions are inherently determined by MRI system parameters such as RF coil sensitivities and the like. Therefore, the sides of such regions are shown by dotted lines in the figures. However, the upper and lower edges of these regions are more precisely determined and critically positioned in space with respect to patient anatomy by the spatially selective RF transmit pulse envelope and frequency spectrum in conjunction with magnitude of the concurrently applied slice select magnetic gradient(s).

For optimal image quality, the patient may be instructed by a recorded voice when to inhale and when to exhale during the entire flow-in balanced SSFP acquisition. For example, the patient's respiratory rate may be regulated to 10 breaths per minute, creating an expiration plateau of approximately 300 msec, during which each data acquisition shot can be executed.

Planning the renal MRA scan typically has in the past required adjusting the tag pulse region, the pre-saturation pulse region (for venous suppression) and a BBTI (black blood time to inversion) time (between the tag pulse and the image data acquisition shot sequence) for every new patient scan. The time to inversion (TI) for STIR (short tau inversion recovery) for fat suppression (or CHESS fat suppression) is, of course, already well known (e.g., about 180 ms at 1.5 Tesla and about 230 ms at 3.0 Tesla) and relatively fixed. This repeatedly required adjustment of tag pulse region, venous suppression pulse region and BBTI parameters for each new patient has presented a rather tedious and cumbersome operation.

Figure 5:
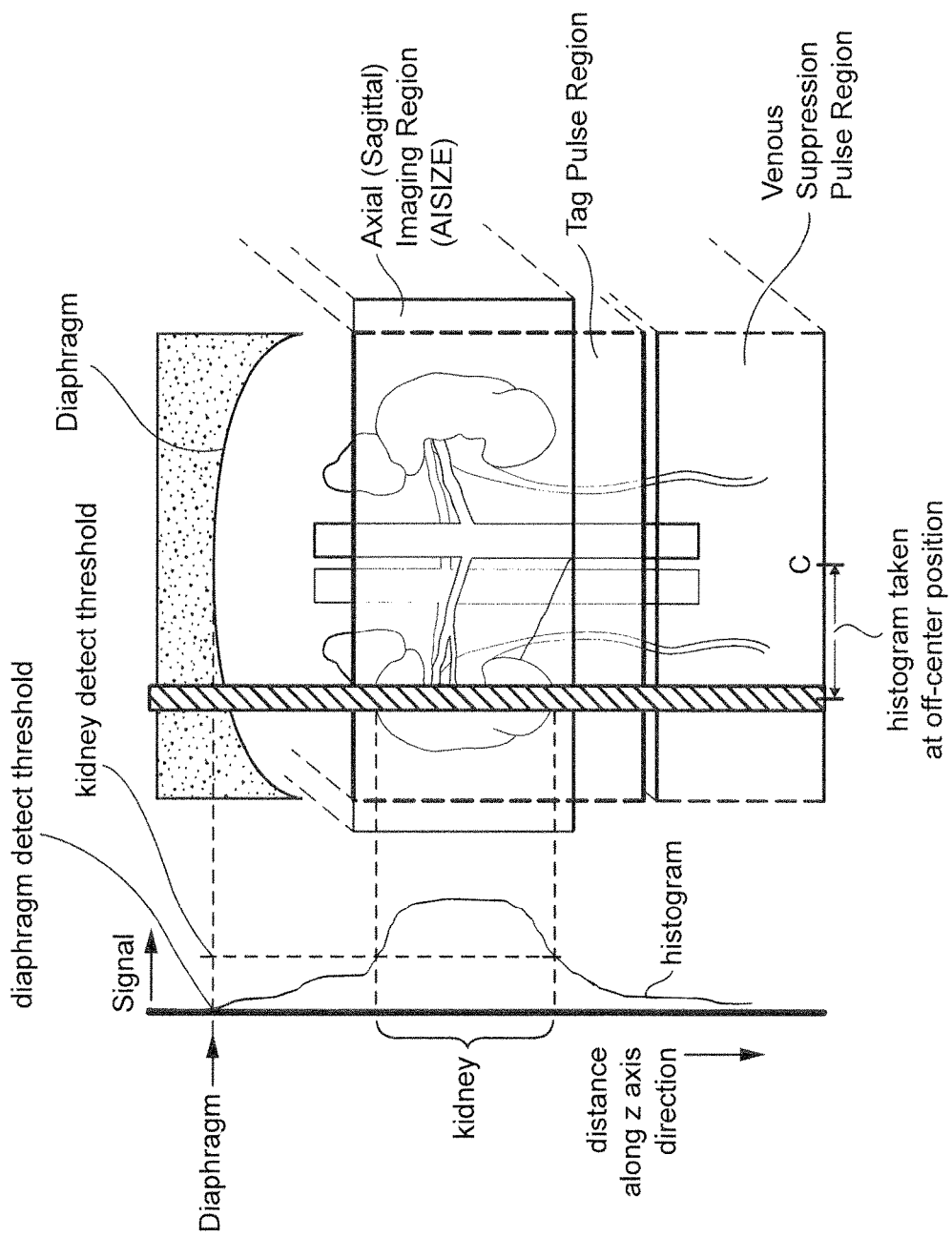
FIG. 5 is similar to FIG. 4, but includes a schematic depiction of an off-center sagittal scout (locator) image histogram that can be utilized for automatically locating the patient kidney and diaphragm anatomy.

Now, however, the exemplary semi-automated non-contrast renal time-SLIP acquisition graphical user interface (GUI) for axial and coronal acquisitions greatly simplifies required operator tasks and reduces operational examination time. The tag pulse region can be placed at a fixed distance from the automatically detected level of the diaphragm (e.g., 5 cm) based on an off-center sagittal histogram (e.g., see FIG. 5) of an initial scout locator image. Because there is essentially no NMR signal from the lung and high NMR signals from the kidneys, preset signal level threshold windows can be used to automatically identify the position of the diaphragm and of the kidneys. For example, especially high amplitude T2-weighted NMR signals emanate from the water-containing kidney tissue. An off-center (e.g., by 5-7 cm) histogram from a sagittal scout image can be used to automatically ascertain the kidney and diaphragm locations. If desired, both left and right off-center histograms can be used to automatically detect a need to rotate the tag and venous suppression pulse regions to accommodate asymmetrical kidney locations.

BBTI also can be automatically calculated by the system from a predetermined formula and/or table (wherein controlling parameters such as patient age, heart rate, etc. are typically already known system parameters by the time MRA imaging is configured by an operator and thus need not be reentered by the operator). For example, the following exemplary table of values can be used:

| Age | BBTI at 1.5 Tesla | BBTI at 3.0 Tesla |
|---|---|---|
| <30 years | 1200 ms | 1300 ms |
| 30-40 years | 1300 ms | 1400 ms |
| 41-50 years | 1400 ms | 1500 ms |
| 51-60 years | 1500 ms | 1600 ms |
| 61-70 years | 1600 ms | 1700 ms |
| 71-80 years | 1700 ms | 1800 ms |
| 81-90 years | 1800 ms | 1900 ms |
| >90 years | 1900 ms | 2000 ms |

BBTI is the blood travel time and BBTI2 is the time between the second tag (venous suppression) and acquisition time. Normally, to suppress the venous signal, BBTI2=approximately 600 ms. If desired, heart rate may also be taken into account. For example, for a 41-50 year old patient, the above table indicates that a BBTI of about 1400 ms at 1.5 Tesla could be set automatically. However, if a higher than expected heart rate and/or less than good pulse quality is determined, then the BBTI may be automatically extended such as shown below:

| Heart Rate (HR) | Pulse Quality | BBTI |
|---|---|---|
| 60-70 per minute | good | 1400 ms |
| 60-70 per minute | weak | 1500 ms |
| 80-90 per minute | weak | 1600-1800 ms |

If a very long TR interval is being used (e.g., TR>>T1 so that the nuclei are substantially all relaxed to their quiescent positions in alignment with the static Bo field at the start of each TR interval), then BBTI might also be roughly calculated using a rough estimation of $t(null)=T1*\ln 2=0.693*T1$.

Functional relationships between age, heart rate, etc. and BBTI can be calculated and/or estimated by suitable closed formulae, as will be appreciated by those in the art.

The venous suppression pulse region position (preset suppression pulse or possibly just another tag pulse with a $2^{nd}$ BBTI time of, e.g., about 600 ms) is placed at a fixed position from the tag pulse region. For example, BBTI may be automatically calculated based on elapsed time from nulling of an inversion pulse at the repetition time (TR)—which may also involve an ECG interval, respiratory gating and navigator gating, as should be apparent to those in the art.

The automatic set-up of tag pulse region position, and/or BBTI time and pre-saturation pulse region position by the MRI system (possibly with operator options for making changes from the initial automatically determined values) makes this exemplary embodiment less cumbersome as compared to earlier methods. From an early locator or scout image, the system can automatically locate and select the patient's diaphragm and kidneys based on contrast (e.g., as established by a suitable learning algorithm and/or predetermined signal level contrast settings) in histogram data collected at one or more off-center location(s) (e.g., about 5-7 cm from the center) in a sagittal scout or locator image (see FIG. 5).

For coronal image acquisition, the position of a coronal multi-slice imaging region (e.g., about 35×35 cm) on the scout image is automatically placed at the diaphragm. The tag pulse region (e.g., an axial length of 25 cm) is automatically placed (e.g., about 5 cm) lower than the diaphragm. The pre-saturation pulse region is automatically placed just below the tag pulse region.

For axial image acquisition, the position of an axial multi-splice imaging region is also automatically set up by the scout image depiction of the diaphragm and kidneys (e.g., about 10 cm below the diaphragm). The tag pulse region (e.g., axial length of 25 cm) is placed automatically about 10 cm lower than the diaphragm. The pre-saturation pulse region is automatically placed just below the tag pulse region.

In brief summary, the semi-automated setting of parameters will be, of course, somewhat different for coronal imaging as opposed to axial sagittal imaging. However, in both instances, the BBTI parameter can be automatically determined (e.g., from a table or formula using age and/or heart rate and/or TR parameters already known to the system). The coronal or axial sagittal tagging pulse region as appropriate can also be automatically positioned at a predetermined fixed distance from the automatically detected patient diaphragm anatomy. Similarly, the venous suppression pulse region is then positioned at a fixed distance from the tagging pulse region.

Preferably, the automatically set positions of these regions (and the automatically determined BBTI) can be visually displayed for the operator to approve—or not if some fine-tuning adjustment is desired by the operator. However, if desired, only a sub-set of these parameters may be automatically determined (and displayed for operator approval/change).

Subsequently, the appropriate coronal or axial sagittal data acquisition processes are performed for the multi-slice coronal or axial sagittal image regions.

For example, the following operational phases may be utilized:
1. Initial scout locator imaging (including sagittal and coronal scout images) is performed.
2. Non-contrast renal time-SLIP scan, axial scan or coronal scan orientation is selected.
3. For a coronal scan, a coronal locator scan image is overlaid by the automatically determined tag pulse region position and venous suppression pulse region position.
4. An appropriate BBTI is automatically determined and displayed. If desired, TR can be determined by the ECG interval, respiratory gating, and/or navigator gating and can be adjusted by the operator.
5. The position of the tag pulse region is calculated from the level of the diaphragm based on at least one sagittal histogram (e.g., where essentially no signal comes from the lung tissue, but high signals come from the kidneys). The level of the tag pulse region can be further adjusted by the operator, if desired.
6. The position of the venous suppression pulse region (either selection of preset pulse region or second tag pulse for the same tag volume, but with a fixed shorter BBTI of around 600 msec) is fixed with respect to the tag pulse region position.

7. The currently set up multi-slice MRI data acquisition sequence shot is executed.

Figure 6:
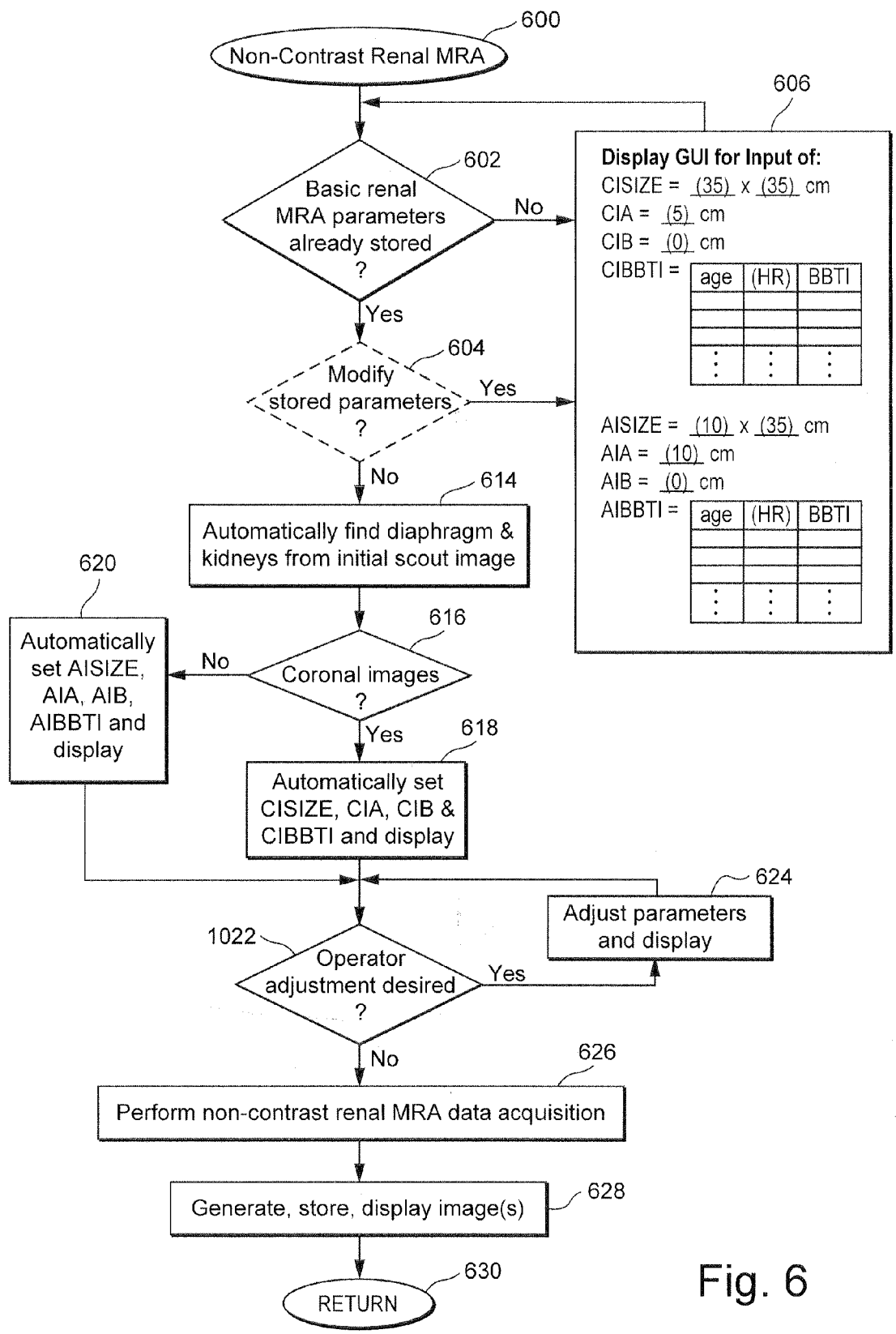
FIG. 6 is a schematic illustration of exemplary computer program code structure in the form of a flow chart for implementing an exemplary embodiment of semi-automated non-contrast renal magnetic resonance angiography.
Figure 7:
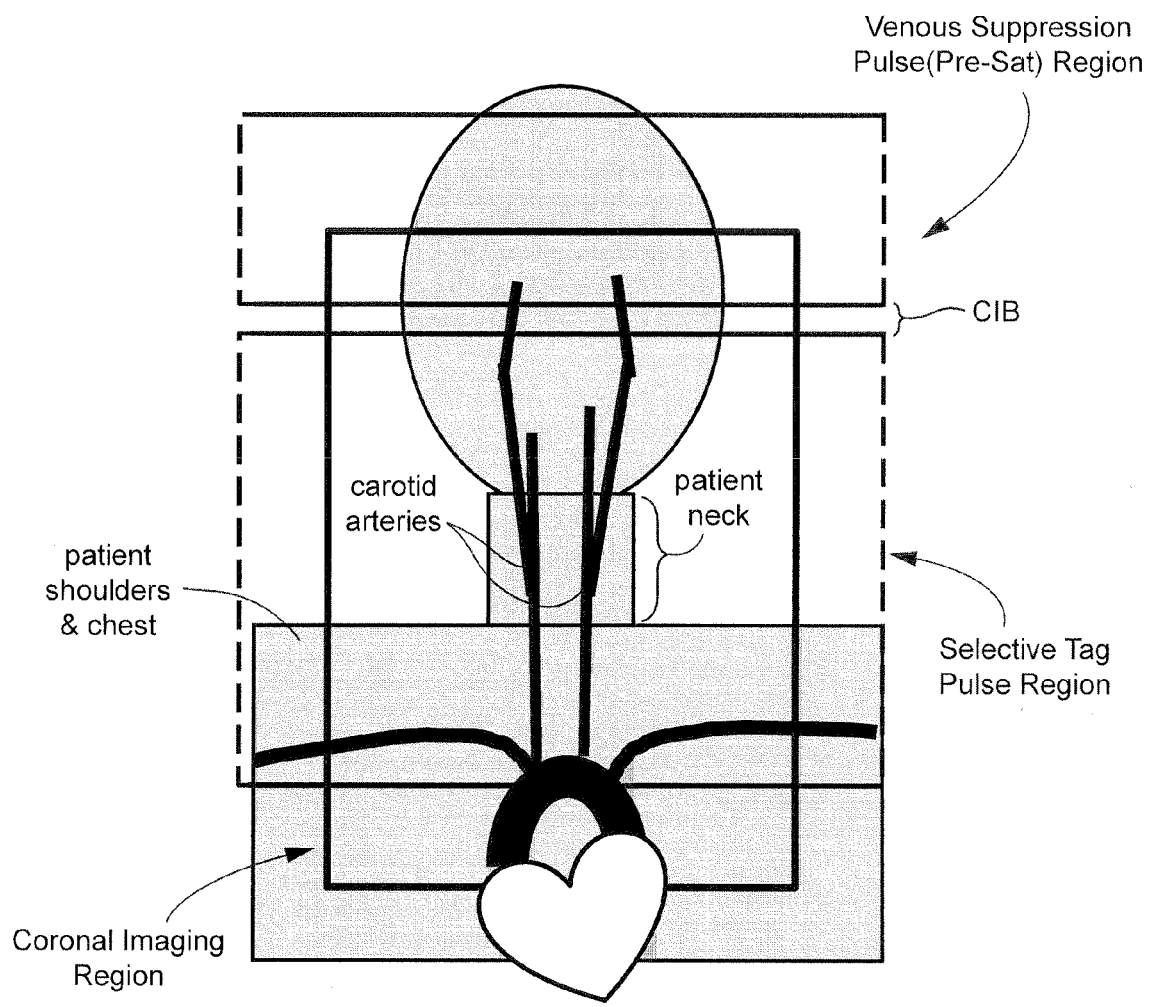
FIG. 7 is a schematic diagram of patient head, neck, shoulder and carotid artery anatomy, as well as tag pulse and venous suppression pulse regions for coronal imaging in accordance with an exemplary embodiment for semi-automated non-contrast carotid artery MRA.

An exemplary computer program code structure is depicted in FIG. 6. Here, a non-contrast renal MRA sub-routine is entered at 600. At 602, a test is made to see whether the basic preset renal MRA parameters are already stored. If so, then, if desired, an option at 604 may be provided where the operator is given an immediate opportunity to modify the stored parameters. Of course, this step may be omitted at this point since a subsequent position for operator adjustment may be provided in this exemplary embodiment.

If the parameters have not already been stored and/or if modification is desired, then step 606 is entered where a graphical user interface (GUI) is displayed for input of preset parameters associated with coronal imaging (CI) and/or axial sagittal imaging (AI). For example, the coronal imaging size (CISIZE) is nominally preset at 35×35 cm. However, the dimensions of this multi-slice imaging region can be modified, of course, if desired, at this point. The coronal imaging dimension A (CIA) between the automatically detected diaphragm and the top of the coronal imaging region is nominally set at 5 cm—but can also be changed, if desired, at this point. The coronal imaging distance B (CIB) between the coronal imaging region and the venous suppression pulse region is preset to zero cm, but, of course, can also be changed at this point.

The coronal imaging BBTI (CIBBTI) may be automatically determined from a preset table (where the age and/or heart rate of the patient should already be available to the system—or may be input at this time if not already available). The heart rate of the patient can, of course, be automatically determined from an ECG signal. Thus, an appropriate BBTI for a particular age (and/or possibly heart rate) may be selected from a table or predetermined formula.

The GUI displayed at 606 also includes parallel parameter setting opportunities for the axial image (AI) parameters AISIZE, AIA, AIB and AIBBTI, as should now be apparent.

In many cases, the test at 602 (and at 604 if included) will result in immediate transfer of control to step 614 where the diaphragm and kidneys of the patient are automatically located from an initial scout image. A test is then made at step 616 to see whether coronal or sagittal images are to be acquired. If coronal images are to be acquired, then control is passed to box 618 where the coronal imaging preset parameters are automatically adopted. On the other hand, if axial sagittal imaging is to be accomplished, then control is passed to box 620 where the axial imaging preset parameters are adopted. Although not required, a final possibility of manual operator adjustment is presented at 622 and, if desired, then suitable adjustments are made at 624. If no further adjustments are desired, then control passes to block 626 where conventional non-contrast renal MRA data acquisition is performed for the multi-slice coronal or axial sagittal imaging regions using the imaging parameters semi-automatically effected by the previous steps in FIG. 6.

Thereafter, an image is generated, stored and/or displayed at 628 before return to the calling higher level module (e.g., an overall MRI operating system) is made at 630.

Another exemplary embodiment, this one for semi-automated carotid artery MRA, is depicted in FIGS. 7-11. This is similar to semi-automated renal MRA, but uses opposite relative positions for the venous suppression (pre-sat) pulse region to suppress venous return signals and a selective tag pulse region—which tag pulse region is now placed to encompass an automatically detected center of the patient neck anatomy. As shown, the venous suppression pulse region is now situated above the tag pulse region by distance CIB (e.g., about 1 cm).

The axial length of the selective tag pulse region (e.g., about 20 to 25 cm or so depending upon patient type) can be defined by distances A and B (above and below neck center) as shown. Alternatively, the shoulder or chin or other automatically detectable patient anatomy may be use as a starting datum for defining the length of the tag pulse region. Note in FIG. 7 that solid lines on the selective tag pulse and pre-sat regions indicate the slice selective direction. The pre-sat pulse region is placed just above the selective tag pulse region. The pre-sat pulse should be, e.g., at least about 1 cm above the selective tag pulse region so as not to interfere with the selective pulse slice profile.

Figure 8:
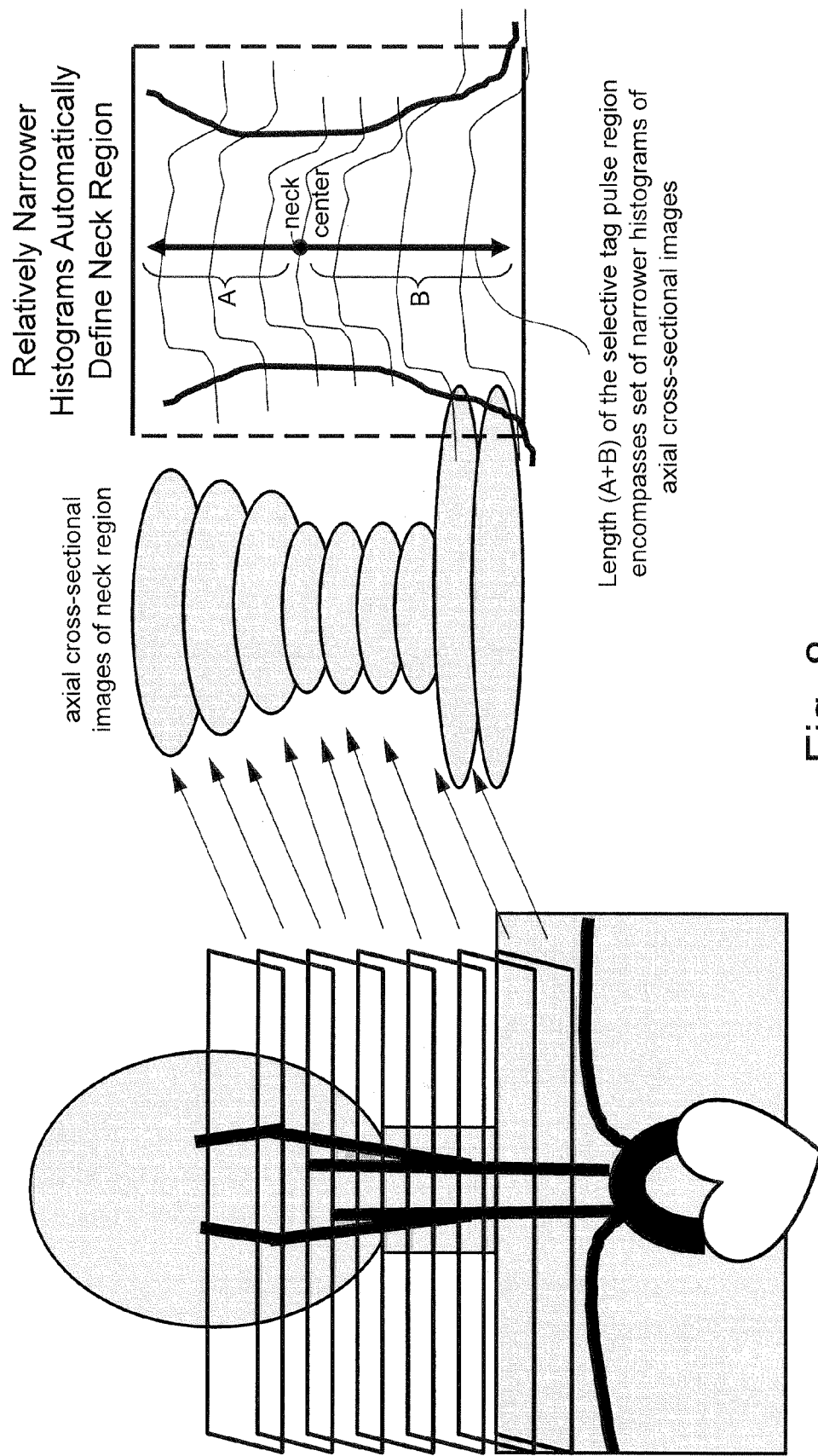
FIG. 8 is similar to FIG. 7, but includes a schematic depiction of plural axial cross-section scout (locator) image histograms that can be utilized for automatically locating the patient shoulder, neck and head anatomy.

Histograms obtained from plural axial images encompassing the neck are acquired and automatically analyzed to detect the center neck anatomy at the center of the narrowest histogram. Histograms obtained from one-dimensional projections of cross-sectional axial images acquired encompassing the neck anatomy can be obtained as depicted in FIG. 8. The tag pulse region can be automatically placed based on the center(s) of the relatively most narrow histograms. The axial length of the selective tag pulse region typically can be about 20-25 cm.

Figure 9:
FIG. 9 presents images of a carotid artery for a health young patient using respectively different BBTI parameter values.

FIG. 9 illustrates carotid artery image examples using various BBTIs for a healthy young volunteer. As can be seen, a BBTI of about 1000-1200 ms may be optimum (although more background clutter is present at 1200 ms). For elder patients, a longer BBTI is required as noted above for renal MRA. Similar BBTIs (1200-1800 ms) can be applied as previously desired for renal MRA due to recovery of the background signal. A 2D/3D acquisition sequence for time-SLIP with bSSFP or FASE would enable depiction of the supra-aortic to carotid arteries.

Figure 10:
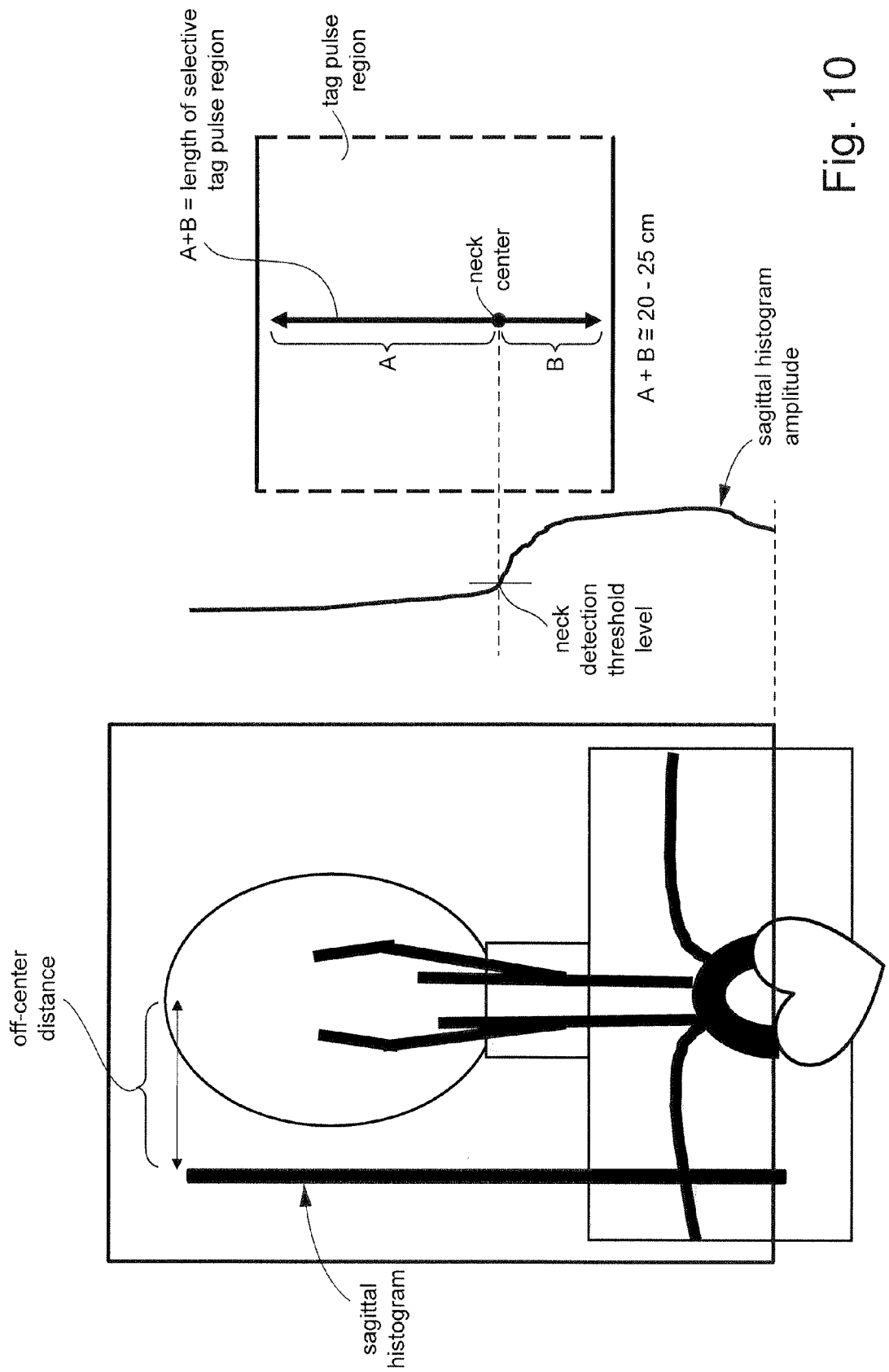
FIG. 10 is an image similar to FIG. 8, but demonstrating how a sagittal scout (locator) image histogram can be used to automatically locate the patient neck anatomy.

Another example for automatic detection of the neck anatomy is schematically depicted at FIG. 10. Here an offset center sagittal histogram is used in conjunction with a neck detection threshold level to find a neck center location. Here, the tag pulse region's axial length A+B is offset vertically so as to encompass more of the patient head anatomy (e.g., to the ears/eye level).

Figure 11:
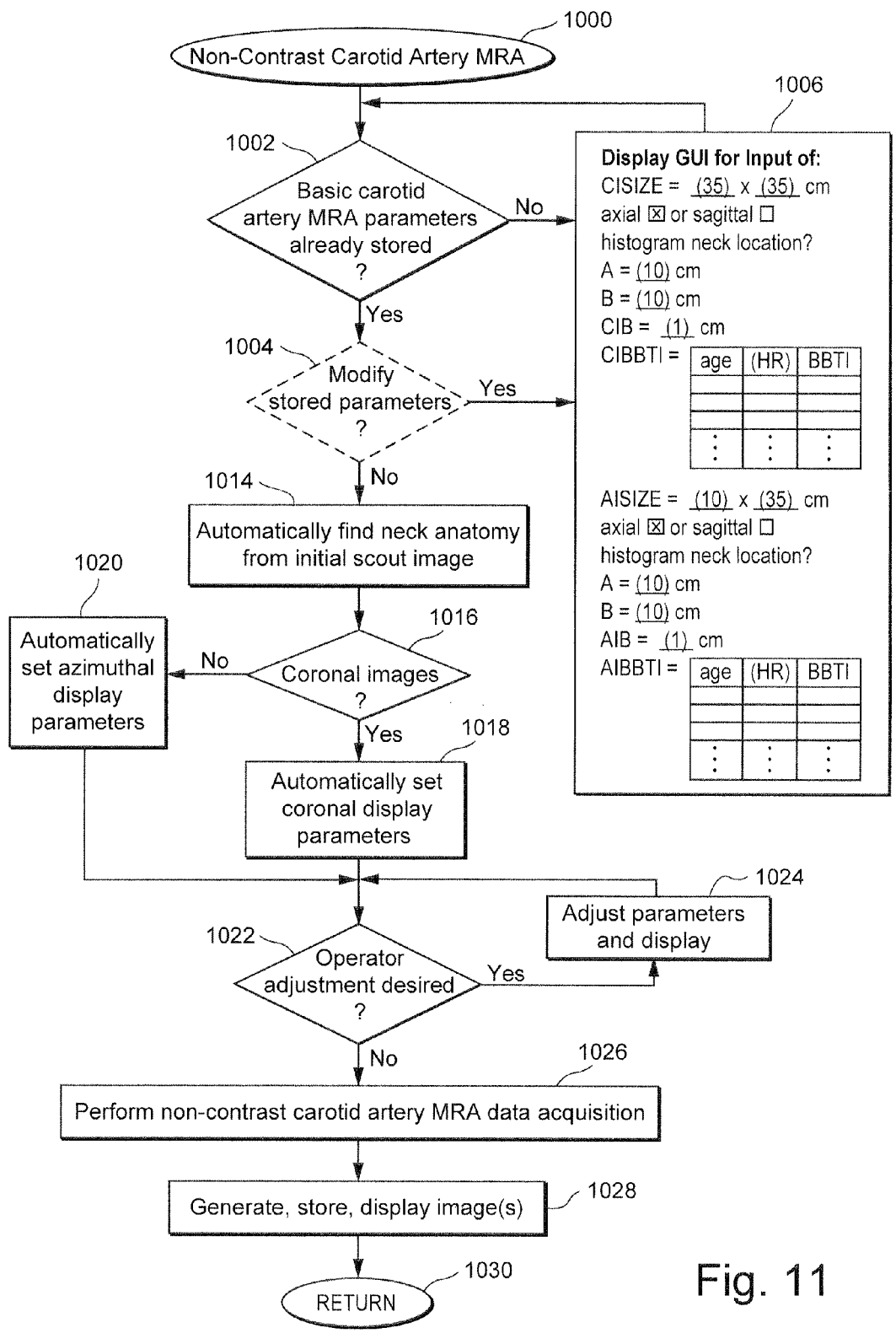
FIG. 11 is a schematic illustration of exemplary computer program code structure in the form of a flow chart for implementing an exemplary embodiment of semi-automated non-contrast carotid artery MRA.

An exemplary computer program code structure for semi-automated carotid artery MRA is depicted in FIG. 11. Here, a non-contrast carotid artery MRA sub-routine is entered at 1000. At 1002, a test is made to see whether the basic preset carotid artery MRA parameters are already stored (e.g., range of narrowest histogram dimensions to be used in automatically detecting the patient neck anatomy). If so, then, if desired, an option at 1004 may be provided where the operator is given an immediate opportunity to modify the stored parameters. Of course, this step may be omitted at this point since a subsequent position for operator adjustment may be provided in this exemplary embodiment.

If the parameters have not already been stored and/or if modification is desired, then step 1006 is entered where a graphical user interface (GUI) is displayed for input of preset parameters associated with coronal imaging and/or axial sagittal imaging. For example, whether axial or sagittal histograms are to be used to locate neck anatomy, the tag region dimensions A+B, the separation CIB between venous suppression and tag pulse regions, BBTI determining parameters, etc., the dimensions of a multi-slice imaging region (in coronal and/or sagittal directions CISIZE and/or AISIZE) can be set and/or modified, if desired, at this point. As shown, the spacing between the preset pulse region and the selective tag region can be nominally preset at 1 cm—but can also be changed, if desired, at this point. The coronal and/or sagittal imaging region(s) can be preset to a certain size or automatically adjusted/set based on the histogram data—but, of course, can also be changed at this point.

As previously noted, the BBTI value(s) may be automatically determined from a preset table (where the age and/or heart rate of the patient should already be available to the system—or may be input at this time if not already available). The heart rate of the patient can be, of course, automatically determined from an ECG signal. Thus, an appropriate BBTI for a particular age (and/or possibly heart rate) may be selected from a table or predetermined formula.

In many cases, the test at 1002 (and at 1004 if included) will result in immediate transfer of control to step 1014 where the neck anatomy of the patient is automatically located from an initial scout image. A test is then made at step 1016 to see whether coronal or sagittal images are to be acquired. If coronal images are to be acquired, then control is passed to box 1018 where the coronal imaging preset parameters are automatically adopted. On the other hand, if axial sagittal imaging is to be accomplished, then control is passed to box 1020 where the axial imaging preset parameters are adopted. Although not required, a final possibility of manual operator adjustment is presented at 1022 and, if desired, then suitable adjustments are made at 1024. If no further adjustments are desired, then control passes to block 1026 where conventional non-contrast carotid MRA data acquisition is performed for the multi-slice coronal or axial sagittal imaging regions using the imaging parameters semi-automatically effected by the previous steps in FIG. 10.

Thereafter, an image is generated, stored and/or displayed at 1028 before return to the calling higher level module (e.g., an overall MRI operating system) is made at 1030.

As should now be appreciated, the exemplary embodiments automatically set tag information such as a tag region position and/or BBTI value(s) based on automatically detected anatomical information (e.g., diaphragm and kidney or neck). Thus, for example, either the tag region position and/or BBTI values may be set. Furthermore, such values may be entirely automatically set—or the setting may be facilitated by providing automatically determined tag position and/or BBTI information for an operator to review and approve/change.

While certain embodiments of the invention have been described, these embodiments have been presented by way of example only, and are not intended to limit the scope of the invention. Indeed, the novel methods and systems described herein may be embodied in a variety of other forms. Furthermore, various omissions, substitutions and changes in the form of the methods and systems described herein may be made without departing from the spirit of the invention. The accompanying claims and their equivalents are intended to cover such forms or modifications as would fall within the scope and spirit of the invention.

What is claimed is:

1. A magnetic resonance imaging (MRI) system configured to perform non-contrast magnetic resonance imaging, said system comprising:
    an MRI gantry including a static magnet, gradient magnet coils and at least one radio frequency (RF) coil defining a patient imaging region into which a patient's anatomical region of interest can be located;
    RF receiver and transmitter circuits coupled to said at least one RF coil; and
    control circuits connected to said gantry and to said RF receiver and transmitter circuits, said control circuits having an operator display and an operator control input port for configuring and operating said MRI system to acquire and process MRI data from said patient,
    said control circuits being configured to control said MRI gantry and said RF receiver and transmitter circuits to perform non-contrast MR imaging by
    acquiring a representation of MR signal versus position of patient anatomy and automatically determining a spatially selective tag pulse region based on the acquired representation of MR signal versus position of patient anatomy and preset signal level threshold.

2. An MRI system as in claim 1, wherein:
    said control circuits are further configured to control said MRI gantry and said RF receiver and transmitter circuits to perform non-contrast magnetic resonance imaging by determining a black blood time interval (BBTI) for a subsequent diagnostic non-contrast MRI data acquisition sequence for a predetermined patient anatomical structure based on a relationship between pieces of patient information and BBTIs, the patient information including at least one of age, a heart rate or a pulse quality of the patient; and
    said control circuits are configured to determine both said spatially selective tag pulse region and said BBTI for said non-contrast MRI data acquisition sequence.

3. An MRI system as in claim 2, wherein:
    said control circuits are configured to automatically display said at least one automatically determined (i) spatially selective tag pulse region and (ii) BBTI in a non-contrast MRI data acquisition sequence and to provide an operator choice for acceptance and/or modification of same.

4. An MRI system as in claim 2, wherein said control circuits are configured to set BBTI based on a predetermined functional relationship between at least patient age and BBTI values.

5. An MRI system as in claim 1, wherein a venous suppression RF pulse region is also automatically determined.

6. An MRI system as in claim 1, wherein said control circuits are configured to detect predetermined patient anatomical structure comprising at least one kidney organ located with respect to a patient diaphragm structure.

7. An MRI system as in claim 1, wherein said control circuits are configured to detect predetermined patient anatomical structure comprising a neck anatomy of the patient.

8. An MRI system as in claim 1, wherein said control circuits are configured to selectively effect said non-contrast MR imaging for either (a) coronal slice images or (b) sagittal axial slice images.

9. An MRI system as in claim 1, wherein said spatially selective tag pulse region is sized and located a predetermined distance inferiorly from a detected level of a patient diaphragm to substantially encompass at least a major portion of patient kidneys to be imaged.

10. An MRI system as in claim 9, wherein said spatially selective tag pulse region is located a predetermined inferior distance from a patient diaphragm that is determined from a sagittal histogram based on a locator scout image wherein higher magnetic resonance signal levels emanate from kidney tissues positioned inferiorly below the diaphragm than from lung tissue positioned superiorly above the diaphragm.

11. An MRI system as in claim 1, wherein said control circuits are configured to locate said spatially selective tag pulse region to substantially encompass at least a major portion of patient neck anatomy to be imaged.

12. An MRI system as in claim 11, wherein said control circuits are configured to size and locate said spatially selective tag pulse region based on a width of plural axial slice histograms of patient anatomy including a neck region.

13. An MRI system as in claim 11, wherein said control circuits are configured to size and locate said spatially selective tag pulse region based on a detected amplitude change in a sagittal histogram of patient anatomy including a neck region.

14. A magnetic resonance imaging (MRI) method for performing non-contrast magnetic resonance imaging, said method comprising:
configuring an MRI gantry and control circuits having an operator display and an operator control input port to acquire and process MRI data from a patient;
acquiring a representation of MR signal versus position of patient anatomy and determining a spatially selective tag pulse region based on the acquired representation of MR signal versus position of patient anatomy and preset signal level threshold; and
performing a non-contrast MRI data acquisition sequence based, at least in part, on said determined spatially selective tag pulse region.

15. An MRI method as in claim 14, further comprising:
determining a black blood time interval (BBTI) for a non-contrast MRI data acquisition sequence for a patient anatomical structure based on a relationship between pieces of patient information and BBTIs, the patient information including at least one of age, a heart rate, or a pulse quality of the patient; and
determining both said spatially selective tag pulse region and said BBTI for said non-contrast MRI data acquisition sequence.

16. An MRI method as in claim 15, wherein:
at least one of said determined (i) spatially selective tag pulse region and/or (ii) BBTI is displayed to an operator for acceptance or change.

17. An MRI method as in claim 15, wherein said BBTI is determined based on a predetermined functional relationship between at least patient age and BBTI values.

18. An MRI method as in claim 14, wherein said predetermined patient anatomical structure comprises at least one kidney organ located with respect to a patient diaphragm anatomical structure.

19. An MRI method as in claim 14, wherein said predetermined patient anatomical structure comprises at least a neck anatomy of the patient.

20. An MRI method as in claim 14, further comprising selectively effecting non-contrast MR imaging for either (a) coronal slice images or (b) sagittal axial slice images.

21. An MRI method as in claim 14, wherein said predetermined tag pulse region is automatically sized and located a predetermined distance inferiorly from a level of a patient diaphragm to substantially encompass at least a major portion of patient kidneys to be imaged.

22. An MRI method as in claim 21, wherein said predetermined tag pulse region is located a predetermined inferior distance from a patient diaphragm that is determined from a sagittal histogram based on a locator scout image wherein higher magnetic resonance signal levels emanate from kidney tissues positioned inferiorly below the diaphragm than from lung tissue positioned superiorly above the diaphragm.

23. An MRI method as in claim 14, wherein said predetermined tag pulse region is sized and located based on widths of plural axial slice histograms of patient anatomy including a neck region.

24. An MRI method as in claim 14, wherein said predetermined tag pulse region is sized and located based on an amplitude change in a sagittal histogram of patient anatomy including a neck region.

\* \* \* \* \*